United States Patent [19]

Ndife et al.

[11] Patent Number: 5,489,440
[45] Date of Patent: Feb. 6, 1996

[54] RICE FLOUR-BASED ORAL REHYDRATION SOLUTION

[75] Inventors: Louis I. Ndife, Columbus; Paul S. Anloague; Rosa C. B. Beach, both of Reynoldsburg, all of Ohio; Michelle M. B. Rushlow, Fort Collins, Colo.; Michael J. Neylan, Columbus, Ohio

[73] Assignee: Abbott Laboratories, Abbott Park, Ill.

[21] Appl. No.: 398,707

[22] Filed: Mar. 6, 1995

[51] Int. Cl.$^6$ ............................ A61K 9/14
[52] U.S. Cl. .................. 424/489; 424/494; 424/498; 424/499; 424/439
[58] Field of Search .................. 424/489, 439, 424/490, 195.1; 514/58, 398, 474

[56] References Cited

U.S. PATENT DOCUMENTS

| | | | |
|---|---|---|---|
| 4,505,926 | 3/1985 | Newsome et al. | 514/398 |
| 4,996,232 | 2/1991 | Gracey et al. | 514/474 |
| 5,096,894 | 3/1992 | Tao et al. | 514/58 |
| 5,120,539 | 6/1992 | Lebenthal | 424/195.1 |

FOREIGN PATENT DOCUMENTS

91/15199 of 1991 WIPO.

OTHER PUBLICATIONS

Patra et al., *Archives of Disease in Childhood*, 57:910–912 (1982).
Molla et al., *Bulletin of the World Health Organization*, 63(4): 751–756 (1985).
Bhan et al., *Journal of Pediatric Gastroenterology and Nutrition*, 6:392–399 (1987).
El Mougi et al., Journal of Pediatric Gastroenterology and Nutrition, 7:572–576 (1988).
Pizarro et al., New England Journal of Medicine, 324:517–521 (1991).
Gore et al., British Medical Journal, 304:287–291 (1992).
Islam et al., Archives of Disease in Childhood, 71:19–23 (1994).

*Primary Examiner*—Thurman K. Page
*Assistant Examiner*—William E. Benston, Jr.
*Attorney, Agent, or Firm*—D. O. Nickey; L. R. Drayer

[57] ABSTRACT

A method for producing an improved rice flour-based oral rehydration solution using the enzymes cellulase and protease is disclosed. The oral rehydration solution of the invention has low viscosity, low osmolality, and can be ingested through the nipple of a bottle. The oral rehydration product can also be dried into powder form before packaging and reconstituted at the time of use. The product is designed to treat individuals with severe diarrhea brought about by cholera or other causes.

17 Claims, 1 Drawing Sheet

PROCESS FOR PRODUCING RICE FLOUR-BASED ORAL REHYDRATION SOLUTION

RICE FLOUR-BASED ORAL REHYDRATION SOLUTION

TECHNICAL FIELD

The present invention relates to an improved oral rehydration solution (ORS) that contains enzymatically treated rice flour. More particularly the invention relates to a stable rice flour oral rehydration solution with low viscosity and low osmolality that can be ingested through the nipple of a bottle. The improved ORS may be in ready-to-feed form or dehydrated to a powder that can be reconstituted at the time of consumption.

BACKGROUND OF THE INVENTION

Diarrhea can be a debilitating disease in both children and adults. In developing countries diseases that result in diarrhea are the largest single cause of death among infants and children. Fluid and weight loss from diarrhea can result in severe dehydration, electrolyte imbalance, and acid-base disturbance.

The development of oral rehydration therapy has reduced morbidity and mortality from acute diarrheal diseases, particularly in less developed countries. Oral rehydration solutions (ORS) typically consist of a mixture of electrolytes and a carbohydrate component such as glucose or sucrose. The World Health Organization (WHO) recommends that oral rehydration solutions contain 20 g of glucose, 3.5 g sodium chloride, 2.5 g sodium hydrogen carbonate, 2.9 g trisodium citrate dehydrate and 1.5 g potassium chloride. These are to be mixed with one liter of water. This and similar glucose-based oral rehydration solutions have provided a simple means for treating or preventing dehydration due to acute diarrhea in infants and children. However, while glucose-based solutions stimulate the intestinal absorption of fluid and electrolytes from isotonic luminal contents, they do not aid in the reabsorption of fluid secreted by the intestine and thus do not lessen the severity of diarrhea. This lack of efficacy in controlling diarrhea constitutes a barrier to global acceptance of oral rehydration therapy and indicates that there is a need for a superior product.

Many studies have indicated that oral rehydration solutions prepared from rice may not only ameliorate dehydration, but may also decrease diarrheal fluid loss and reduce stool output. Rice is cheap, safe, and easily obtained and eaten by a large fraction of the world population. However, rice, as used in several studies discussed below, has some disadvantages including the need for cooking, the possibility of incorrect preparation, its relative insolubility in liquid resulting in rapid precipitation after mixing, and the need for it to be spoon fed to infants. The rice-based oral rehydration solution of the instant invention, produced through a process that utilizes enzymatic digestion of the cellulose and protein fractions of rice flour, retains the advantages of a rice-based solution and overcomes these disadvantages.

Patra et al., (*Archives of Disease in Childhood*, 57:910–912, 1982) demonstrated in a controlled trial of oral rehydration therapy for infants and young children with acute diarrhea the superiority of a rice-based oral solution to the WHO recommended glucose electrolyte solution as shown by a lower rate of stool output, a shorter duration of diarrhea, and a smaller intake of rehydration fluid. In the solution of Patra et al. glucose was replaced by "pop rice" powder. Pop rice, which is commonly consumed in the Indian subcontinent, is prepared by popping unhusked rice on heated sand. In this study the pop rice was made into powder form and dissolved in the rehydration fluid before use. The rehydration solution was fed by cup and spoon or directly from a cup. Thus, although the efficacy of a rice-based solution was demonstrated, the methods of preparation and delivery had the disadvantage of requiring on-site activity by the person feeding the patient.

In a randomized trial of children and adults suffering from cholera or cholera-like diarrhea, Molla et al., (*Bulletin of the World Health Organization*, 63(4):751–756, 1985) found that rice-based oral rehydration solutions decreased the stool volume more effectively than glucose or sucrose oral rehydration solutions. In this study, rice powder was boiled in water to produce a colloidal suspension. After cooling, electrolytes were added to the gruel mixture. The mixture had to be prepared shortly before administration and was fed to patients by their attendants.

Bhan et al., (*Journal of Pediatric Gastroenterology and Nutrition*, 6:392–399, 1987) found a trend toward improvement in efficacy, as measured by recovery from diarrhea with 72 hours, with pop rice ORS as compared with the standard glucose electrolyte solution or with a mung bean solution in children suffering from acute diarrhea caused predominantly by rotavirus or *Escherichia coli*. In this study rice was obtained from the local market and made into powder form before use. It was then mixed in boiled water, and given to the mother to be fed by cup and spoon.

In a controlled clinical trial with infants with acute diarrhea El-Mougi et al., (*Journal of Pediatric Gastroenterology and Nutrition* 7:572–576, 1988) demonstrated the efficacy of rice powder-based oral rehydration solutions. Rice powder and salts were placed in packets and dissolved in hot water and stirred at the time of utilization. It was then cooked until a gel was formed, cooled, and consumed warm in a semi-liquid form. It was determined that the rice powder-based ORS did not ferment before 24 hours even without refrigeration. Outcome measurements, including watery stool output, showed that rice ORS is at least as good, and possibly better than glucose ORS therapeutically and nutritionally. The authors concluded by advocating additional food technology research to make a rice enriched ORS ready for use by mothers who do not read directions well. The present inventors have produced such a product.

Results of a clinical trial reported by Pizarro et al., (*New England Journal of Medicine* 324:517–521, 1991) indicated that stable, ready-to-use commercially prepared rice-based oral electrolyte solutions containing rice-syrup solids were more efficient than glucose-based solutions in promoting fluid and electrolyte absorption during rehydration in infants with acute diarrhea. This study demonstrates the utility of a rice-based, ready-to use commercially prepared ORS. However, the rice-based ORS of this study contained only rice glucose polymers, not whole rice, unlike the present invention, and the solution was not produced by the method of the present inventors.

Gore et al., (*British Medical Journal* 304:287–291, 1992) undertook a meta-analysis of clinical trials that compared the benefit of rice oral rehydration salts solutions with the glucose-based WHO oral rehydration salts solution for treating and preventing dehydration in patients with severe dehydrating diarrhea. Using stool output during the first 24 hours as the main outcome measure they found that rice solution significantly reduces stool output in adults and children with cholera and to a lesser extent reduces the rate of stool loss in infants and children with acute non-cholera diarrhea. This meta-analysis serves to confirm the results of previous individual trials of rice-based solutions, thereby underscoring the desirability of producing a product that delivers a rice-based ORS in a commercially available, safe, and easily ingested form as was done by the present inventors.

Islam et al., (*Archives of Disease in Childhood* 71:19–23, 1994) conducted a prospective, randomized controlled trial to evaluate the efficacy and digestibility of rice-based oral rehydration therapy in infants less than 6 months old compared with WHO ORS. The results of this trial support the hypothesis that rice oral rehydration therapy can be safely and effectively used in the management of acute diarrhea in infants younger than 6 months. These findings are consistent with the results of previous studies, discussed above, conducted with older children and adults.

Tao et al.(U.S. Pat. No. 5,096,894) disclose a ready-to-use ORS comprising a mixture of rice dextrin and electrolytes and a process for clarifying rice dextrins. Rice dextrins are rice syrup sugars containing glucose polymers of varying lengths. By contrast the present inventors use rice flour obtained from ground rice in the preparation of a ready-to-use ORS or an ORS in powdered form. Tao et al. teach that rice flour is not suitable as a carbohydrate component for a clear, shelf-stable, ready-to-use ORS because of its insolubility, product appearance, and problems associated with sterilization. These problems have all been successfully solved in the instant invention, which has the additional attribute of being nipple feedable.

Lebenthal (U.S. Pat. No. 5,120,539, WO 92/12721) discloses a method for treating diarrhea in infants by administering a solution containing a complex carbohydrate that has been hydrolyzed by α-amylase. Rice powder is one of the carbohydrates that can be used in preparing the diarrhea treatment product disclosed by Lebenthal. Lebenthal does not address problems of osmolality and the propensity of the powder to precipitate out of solution. By contrast, the instant invention results in a stable product of low osmolality capable of being ingested through the nipple of a bottle.

Shacknai et al. (WO 91/15199) disclose a composition for treating diarrhea that is suitable for children and adults and comprises a nutritional substance, a synthetic fiber, and electrolytes. Rice flour is one of the nutritional substances that can be used in this composition. Method and conditions of production are not taught, nor is product stability or viscosity addressed.

An object of the present invention is to provide a ready-to-use ORS containing rice flour in a stable form with low osmolality and low viscosity suitable for delivery to infants through the nipple of a bottle, or a powdered form of the product that can be reconstituted before use and that has the same desirable properties. A further object of the present invention is to provide an improved rice flour based ORS that results in lower net fluid intake and reduced stool output during the rehydration period of treatment of children with dehydration caused by acute diarrhea.

SUMMARY OF THE INVENTION

Figure 1:
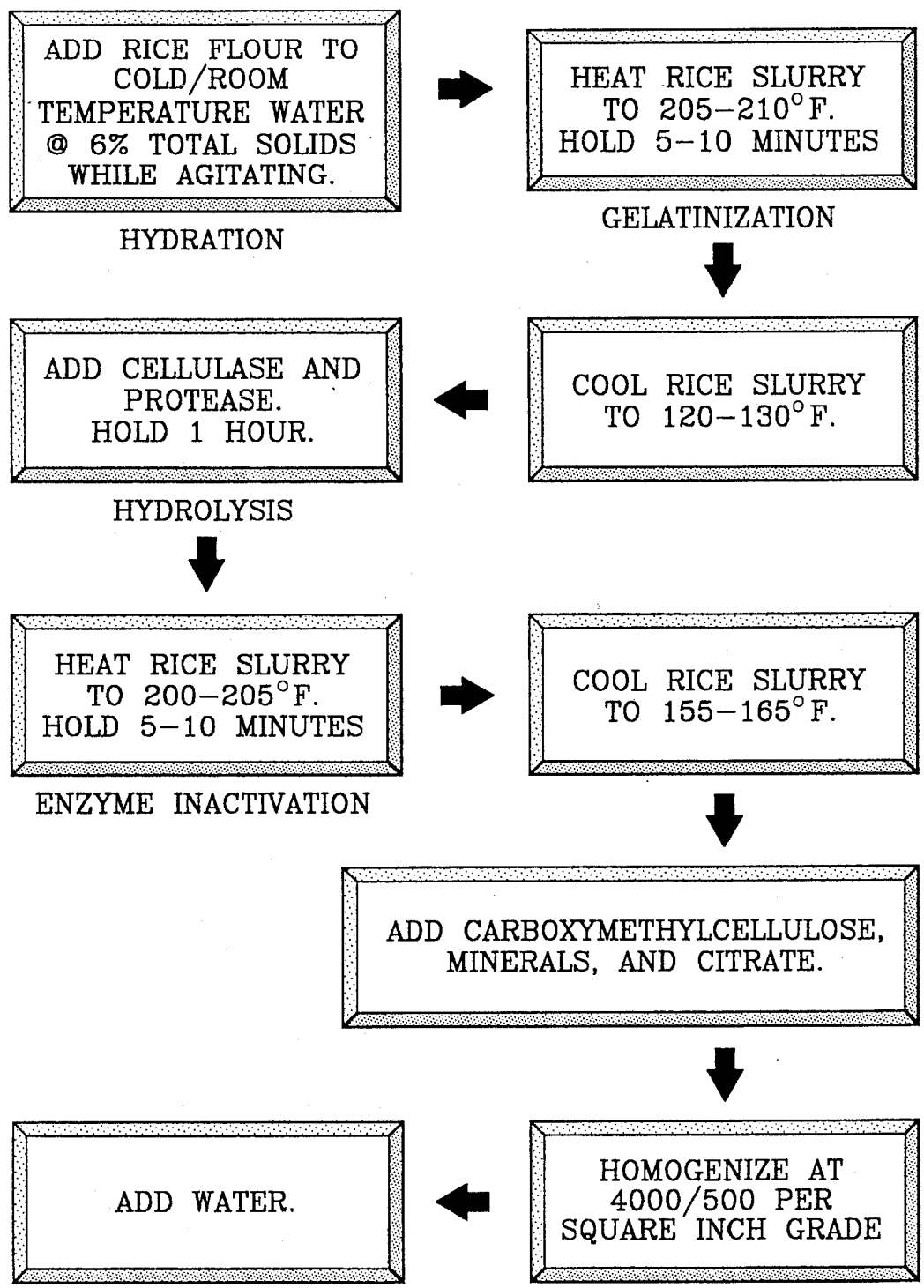
FIG. 1 is a flow diagram of the process for producing the rice flour-based solution of the invention.

The present invention provides a product, a rice flour-based solution for oral rehydration therapy, and a process for preparing a product comprising enzymatic digestion of rice flour and addition of a stabilizer and electrolytes. The product may additionally be sweetened with Aspartame® or any other suitable artificial sweetener. The process of the invention results in a rice-flour based ORS that is stable, has low osmolality and low viscosity, and can be administered to an infant through a nipple. The product was terminally sterilized, making it microbiologically safe and ready-to-use. The product can, in another embodiment be dried, sterilized, and packaged in powder form to be reconstituted at the time of use.

There is disclosed a process for producing an oral rehydration solution containing electrolytes and rice flour comprising the steps of adding rice flour to water while agitating to produce a rice slurry; gelatinizing the rice slurry by heating; cooling the slurry sufficiently to permit enzymatic hydrolysis; adding the enzymes cellulase and protease to the slurry and allowing enzymatic digestion to occur for a period of time sufficient to permit hydrolysis of the rice flour; inactivating the enzymes with heat and then cooling the slurry; adding a stabilizer, minerals, and citric acid; homogenizing the slurry; standardizing the solution by adding water; and terminally sterilizing the product. There is further disclosed a process for drying the oral rehydration solution into a powder. There is further disclosed an oral rehydration product produced by the process for producing an oral rehydration solution and an oral rehydration product produced by the process for producing an oral rehydration solution where the product is dried into a powder. There is further disclosed a method of treating an individual requiring oral rehydration comprising feeding the individual a therapeutically effective amount of the oral rehydration product produced by the disclosed process.

Representative of the stabilizers useful in the present invention are carboxymethylcellulose (CMC), carrageenan, and gum arabic. CMC is the preferred stabilizer. Potassium chloride, sodium citrate, citric acid, and sodium chloride are representative of the electrolytes useful in the present invention. One skilled in this art will appreciate that various substitutes can be made. Neutrase® (a protease) and cellulase are representative of the enzymes useful in the present invention. Enzymes for digestion of rice flour protein and cellulase are available from various suppliers. Aspartame® is representative of the sweeteners useful in the present invention that may optionally be added. Strawberry, fruit punch, banana bubble gum, blue raspberry, and lemon cream are representative of artificial flavors that can be optionally added.

DETAILED DESCRIPTION OF THE INVENTION

EXAMPLE I

Rice flour is made from rice kernels that have been boiled, dehusked, and ground. The rice flour-based oral rehydration solution of the present invention was prepared by first adding rice flour to cold or room temperature water while agitating until the mixture contains 6% total solids. To gelatinize the mixture the rice slurry was heated to 205°–210° F. (96°–99° C.) for 5 to 10 minutes and allowed to cool to 120°–130° F. (49°–55° C.) for enzymatic digestion. To hydrolyze the rice flour, a cellulase and protease were added and hydrolysis was allowed to proceed for a period of time that varies depending on the amount of enzyme added. When cellulase was added at 1% by weight of the fiber content of the rice flour and protease was added at 3% by weight of the protein content of the rice flour, one hour was required for hydrolysis. One skilled in the art will be able to determine the enzyme concentrations and hence the time required for hydrolysis under different conditions. The enzymes were inactivated by heating the slurry to 200°–205° F. (94°–96° C.) for 5 to 10 minutes. The slurry was then cooled to 155°–165° F. (68°–74° C.). Carboxymethylcellulose (CMC), minerals and citric acid were added and the solution was homogenized at 4000/500 PSIG (27579.028/3447.3785 kPa). Concentrations of the components was brought to the desired dilution by the addition of water. Flavor and coloring solutions were optionally added. The solution can also be dried to a powder. FIG. 1 is a flow diagram of the process for producing a rice flour-based solution for oral rehydration therapy. The contents of the rice flour-based oral rehydration solution of this Example are shown in Table 1.

TABLE 1

Rice Flour-Based Oral Rehydration Solution

| Ingredients | Total Yield lbs/1000 lbs | kg/ 453 kg |
| --- | --- | --- |
| Water | 941.00 | 426.27 |
| Rice Flour (Riviana Rice, Houston, TX) | 49.00 | 22.20 |
| CMC | 4.81 | 2.18 |
| Potassium Chloride | 1.55 | 0.70 |
| Sodium Citrate | 1.36 | 0.62 |
| Citric Acid | 1.12 | 0.51 |
| Sodium Chloride | 0.83 | 0.38 |
| Neutrase ® (Novo-Nordisk, Bagsvaerd, DK) | 0.25 | 0.11 |
| Cellulase (Solvay Enzymes, Elkhart, IN) | 0.10 | 0.05 |
| Flavors/Colors | Optional | |

It is known that adding rice in some form to an oral rehydration solution that contains electrolytes results in lower stool volume in patients suffering from acute diarrhea. The problem confronting the present inventors was to develop an ORS containing rice that could be commercially prepared so that it would not have to be mixed at the time of use, would be stable so that rice would not precipitate out of solution, had low osmolality, and could be ingested through the nipple of a bottle so that it did not have to be spoon fed to an infant. The product produced by the method of the present invention meets these criteria.

The following experiments illustrate the critical features determined during the development of the invention.

Experiment 1: Hydration of Rice Granules

Medium grain rice flour ground to 200 U.S. mesh size (RM-200) for use in the ORS of the invention was obtained from Riviana Rice (Houston, Tex.) and added to cold or room temperature water until the resulting rice flour slurry contains total solids in the range of 2 to 7%. Total solids should be within this range in order to optimize two requirements for a useful product. Water is normally absorbed from the digestive tract into cells of the large intestine and colon. Failure of the cells of the large intestine or colon to absorb water from the digestive tract can result in diarrhea, which can lead to dehydration and ion loss. Glucose is normally cotransported with sodium during the active transport of sodium ions. This is accompanied by the diffusion of water into the cells from the lumen of the gut, a necessary process in the prevention or recovery from diarrhea. If total solids constitute less than 2% of the slurry, not enough glucose will be available to be cotransported with sodium ions from the digestive tract into the cells. This results in insufficient reabsorption of sodium and suboptimal reabsorption of water from the lumen into the cells of the gut. If total solids constitute more than 7% of the slurry, there will be insufficient water to fully hydrate the rice granules. A preferred range of total solids is between 5 and 6%, with the most preferred being 6%.

Experiment 2: Gelatinization of Rice Slurry at Critical Temperature

The rice slurry, which was at room temperature, was heated to between 205° and 210° F. (96°–99° C.) and held at a temperature within this range for between 5 and 10 minutes. It is critical for the practice of the invention that the temperature be maintained at 202° F. (94.4° C.) or higher and preferably within the range 205°–210° F. (96°–99° C.) during the gelatinization period. Before arriving at the critical temperature, the inventors experimented with temperatures of 180° and 195° F. (82° and 94.9° C.). At these temperatures the rice granules were not adequately gelatinized, and consequently the product did not have the desired characteristic of low viscosity that would permit nipple feeding.

Experiment 3: Hydrolysis

The gelatinized rice slurry was cooled to between 120° and 130° F. (49°–54.4° C.) for enzymatic hydrolysis. As shown in Table 2 various combinations of hydrolyzing enzymes were tried before determining that a cellulase and a protease were the preferred enzymes for use in the invention. The cellulase and protease may be added simultaneously or sequentially, and either can be added first.

TABLE 2

| Treatment | Viscosity (mPa s*) |
| --- | --- |
| No enzyme | 46 |
| Protease | 15 |
| Cellulase | 20 |
| Protease + cellulase | 9.1 |
| α-amylase | 8.5 |
| Cellulase + α-amylase | 8.4 |
| Protease + α-amylase | 7.6 |
| Protease + cellulase + α-amylase | 6.5 |

*Viscosity values are in units of millipascal seconds (mPa s), which is equivalent to centipoises (cp)

The combination of amylase plus cellulase plus protease resulted in the least viscosity. That combination, however, had high osmolality, which is an undesirable characteristic for the treatment of diarrhea as osmotic pressure will result in the flow of water into the intestine. When amylase was eliminated, the resulting combination of cellulase plus protease had the desirable characteristics of low osmolality and low viscosity.

In the preferred embodiment Cellulase AC (Solvay Enzymes, Elkhart, Ind.) and Neutrase® (Novo-Nordisk, Bagsvaerd, DK) were added to the slurry to hydrolyze the rice and the hydrolysis was allowed to proceed for one hour. The slurry was then heated to between 200° and 205° F. (94°–96° C.) for 5 to 10 minutes in order to inactivate the enzymes. It was determined that a one hour hydrolysis resulted in polymers of a size best suited for a product of low viscosity and low osmolality. After the enzymes were inactivated the slurry was cooled to between 155° and 165° F. (68.5°–74° C.).

Experiment 4: Stabilizer, Minerals, and Citric Acid

Carboxymethylcellulose (CMC) was added as a stabilizer. A study was done to determine the optimal level of CMC for the rice flour-based ORS. CMC was added to the product at the following levels: 0.2%, 0.3%, 0.4%, 0.5%, 0.8% of the total weight of the final product. Results indicated that the level of CMC must be not less that 0.3% in order for the product to remain stable and homogenous for at least 4 hours. The maximum amount of CMC permitted by the FDA in food products is 0.8%, therefore, stability and homogeneity were tested up to that point only. Stability and homogeneity of the product at the 0.5% level were found to be as good as at the 0.8% level and were slightly better than at the 0.3% level. Therefore, in the most preferred embodiment 0.5% CMC was added as a stabilizer.

Experiments were performed to determine the preferred stabilizer. Carrageenan, in both the iota and kappa form, and gum arabic were tested at the 0.5% level and compared with CMC. The product had less physical stability as measured by phase separation when carrageenan or gum arabic were used. The most preferred stabilizer that best prevented phase separation within four hours was determined to be CMC.

Potassium and sodium salts and citric acid were added as shown in Table 1 and comply with WHO recommendations for oral rehydration solutions. Citrate is required in order to maintain the acid:base balance. Mineral salts and citric acid were added within clinically accepted ranges.

Experiment 5: Homogenization and Standardization

The product was homogenized at 4000/500 PSIG (pressure per square inch gauge) (27579.028/3447.3785 kPa) at a temperature between 160° and 170° F. (71°–77° C.) and then cooled. The product was made ready for packaging with the addition of enough water to bring total solid content of the product to between 5.0 and 5.5%.

Experiment 6: Production of Powdered Rice Flour-Based Product and Reconstitution A known volume of the ready-to-feed product from Example I was freeze-dried completely to a powder. To reconstitute the product into a ready-to-feed solution, fresh, clean water was added at a volume equivalent in volume to the volume before freeze-drying.

The product produced by the process described above, both in its original ready-to-feed form or in its reconstituted form has low osmolality, which is desirable for water retention, and low viscosity so it can be fed to infants through the nipple of a bottle.

The following example illustrates the use of the invention in the treatment of acute diarrhea in children.

EXAMPLE II:

Clinical Comparison of Rice Flour-Based ORS with Glucose ORS

Oral electrolyte solutions currently used in the United States and the solution distributed by the WHO contain glucose as the carbohydrate source. Glucose-based solutions are effective in replacing fluid and electrolytes lost during acute diarrhea, but are ineffective in controlling stool volume or the duration of diarrhea. Oral rehydration solutions containing alternative carbohydrate sources, such as the rice flour of the present invention or other cereals, are intended to be an improvement in that they not only replace fluid and electrolytes but also decrease stool volume, reduce duration of diarrhea, and may have some nutritive value. The greatest efficacy has been shown to be solutions to which rice flour was added. However, because rice flour is relatively insoluble previously used solutions, as discussed above, had to be mixed and consumed by spoon feeding at the time of administration.

The present inventors have developed a rice flour-based solution in which the rice flour remains in suspension and has the added beneficial characteristics of low osmolality and low viscosity. A clinical study was carried out to evaluate the efficacy of the rice flour-based rehydration solution of the present invention when compared with a glucose-based ORS.

Children aged 3 to 24 months who presented with acute diarrhea, defined as three or more watery stools within 24 hours, were eligible for enrollment. Enrolled children were randomized to receive either a glucose-based ORS (Rehydralyte®, Ross Products Division, Abbott Laboratories, Columbus, Ohio) or the rice-flour based solution of the invention. It is envisioned that 100 children will eventually be enrolled. Data from the first 56 patients to complete the study were analyzed and are presented here. The inventors will amend this specification when the study has been completed.

Patients were rehydrated with either the glucose-based (Rehydralyte®) or the rice-based ORS of the invention, which has an electrolyte composition like that of Rehydralyte®. After rehydration, when the fluid deficit had been replaced, the control group that had received the glucose-based solution was given a standard maintenance solution (Pedialyte®, Ross Products Division, Abbott Laboratories, Columbus, Ohio) and the experimental group that had received the rice-based solution was continued on a rice-based solution that had an electrolyte composition similar to Pedialyte®. Both groups were also fed with Isomil® (Ross Products Division, Abbott Laboratories, Columbus, Ohio), a soy-based infant formula.

A 48 hour fluid balance study was conducted to determine the volume of intake and stool losses. Fluid intake and losses due to either vomiting or stool output were determined by weighing the feeding containers before and after feeding, diapers before and after stool, and diapers placed under the patient's head to collect vomitus. Duration of diarrhea was also recorded.

Patient characteristics are shown in Table 3. The mean age of the subjects in the rice flour group and, consequently, their weights were significantly greater than in the Rehydralyte® group.

TABLE 3

| Characteristics of Patients on Admission (Mean ± SEM) | | |
| --- | --- | --- |
| | Rehydralyte ® | Rice flour-based ORS (Invention) |
| No. of Patients | 29 | 27 |
| Age at Admission (months) | 12 ± 1[a] | 15 ± 1[b] |
| Weight (kg) | 8.6 ± 0.2[a] | 9.4 ± 0.3[b] |
| Duration of Diarrhea Prior to Admission (days) | 2.0 ± 0.2 | 1.9 ± 0.2 |
| Number of Stools in Previous 24 hrs (Mean ± SEM) | 12 ± 1 | 10 ± 1 |
| Degree of Dehydration | | |
| Mild | 15/29 (52%) | 19/27 (70%) |
| Moderate | 14/29 (48%) | 8/27 (30%) |
| Vomiting on Admission | 20/25 (80%) | 19/26 (73%) | a < b, P < 0.05

Fluid intake and stool output are shown in Table 4. During the first six hour of the study, fluid intake and stool output were significantly less, using parametric analysis, in the rice flour group when compared with the Rehydralyte® group. Although the trend was similar during other study periods, the differences were not statistically significant. These preliminary results suggest that a rice-based ORS solution of the kind produced by the process of the invention is clearly advantageous during the first six hours when treating children suffering from dehydration secondary to acute diarrhea and may continue to be similarly advantageous during for the following 42 hours of treatment.

TABLE 4

Fluid Intake and Stool Output (Mean ± SEM)

|  | Rehydralyte ® | Rice Flour ORS (Invention) |
|---|---|---|
| Net Fluid Intake* (mg/kg/day) | | |
| 0–6 hours | 139 ± 11[a] | 110 ± 8[b] |
| 6–12 hours | 89 ± 11 | 75 ± 9 |
| 12–24 hours | 138 ± 19 | 108 ± 10 |
| 24–48 hours | 212 ± 36 | 187 ± 22 |
| Stool Output (g/kg/day) | | |
| 0–6 hours | 64 ± 10[a] | 41 ± 7[b] |
| 6–12 hours | 44 ± 6 | 45 ± 10 |
| 12–24 hours | 86 ± 15 | 62 ± 8 |
| 24–48 hours | 116 ± 30 | 90 ± 18 |

*Total Fluid Intake minus vomiting
a > b, $P < 0.05$

Industrial Applicability

Previous studies have shown that oral rehydration solutions prepared from rice may be superior to glucose-based oral rehydration solutions in ameliorating dehydration and reducing stool output in individuals suffering from severe diarrhea. To be optimally useful the product must have the property of low osmolality. Previous formulations, however, suffered from the need to be prepared on-site and from the requirement that they be consumed either from a cup or fed by spoon. These presented problems of hygiene and administration. In one embodiment the present invention eliminates the need for on-site preparation and cup or spoon feeding by delivering a microbiologically safe product in liquid form that, because of its property of low viscosity, can be consumed by an infant through the nipple of a bottle. The low osmolality of the present invention alleviates the problem of fluid loss that accompanies severe diarrhea. In an alternative embodiment the product prepared according to the method of the invention is dried and must be reconstituted at the time of use. When reconstituted it still possesses low viscosity and, hence, the desirable property of being able to pass through the nipple of a bottle.

The method described herein constitutes preferred embodiments of this invention. However, the invention is not limited to this precise form of the method and changes may be made without departing from the scope of the invention, which is defined in the appended claims.

What is claimed is:

1. A process for producing an oral rehydration solution containing electrolytes and rice flour comprising the steps of:

(a) adding the rice flour to water while agitating to produce a rice slurry;

(b) gelatinizing the rice slurry by heating;

(c) cooling the slurry sufficiently to permit enzymatic hydrolysis;

(d) adding the enzymes cellulase and protease to the slurry and allowing enzymatic digestion to occur for a period of time sufficient to permit hydrolysis of the rice flour;

(e) inactivating the enzymes with heat and then cooling the slurry;

(f) adding a stabilizer, minerals, and citric acid;

(g) homogenizing the slurry;

(i) standardizing the solution by adding water; and (j) terminally sterilizing the product.

2. The process according to claim 1 wherein the rice flour is added to cold or room temperature water to produce a rice slurry containing 2–7% total solids.

3. The process according to claim 1 wherein the rice slurry is gelatinized by heating to a temperature of at least 202° F. (94.4° C.) for between 5 and 10 minutes.

4. The process according to claim 3 wherein the rice slurry is gelatinized by heating to between 205° and 210° F. (96°–99° C.).

5. The process according to claim 1 wherein the gelatinized rice slurry is cooled to between 120° and 130° F. (49°–54.4° C.) and the enzymes are added thereafter.

6. The process according to claim 1 wherein the enzymes are inactivated after hydrolysis at a temperature between 200° and 205° F. (94°–96° C.) for 5 to 10 minutes.

7. The process according to claim 1 wherein the slurry is cooled to between 155° and 165° F. (68.5°–74° C.) before adding the stabilizer, minerals, and citric acid.

8. The process according to claim 7 wherein the stabilizer is selected from the group consisting of carboxymethylcellulose (CMC), carrageenan, and gum arabic.

9. The process according to claim 8 wherein carboxymethylcellulose is added at 0.3%–0.8% of the total weight of the final product.

10. The process according to claim 8 wherein carboxymethylcellulose is added at 0.5% of the total weight of the final product.

11. The process according to claim 7 wherein the minerals are selected from the group consisting of potassium chloride, sodium citrate, and sodium chloride.

12. The process according to claim 1 wherein the slurry is homogenized at 4000/500 PSIG (27579.028/3447.3785 kPa).

13. The process according to claim 1 further comprising drying the solution into a powder.

14. An oral rehydration product produced by the method of claim 1.

15. The oral rehydration product according to claim 14 wherein the product is dried into a powder.

16. A method of treating an individual requiring oral rehydration comprising feeding the individual a therapeutically effective amount of the oral rehydration product of claim 1.

17. A method of treatment according to claim 16 further comprising feeding through the nipple of a bottle.

* * * * *